United States Patent
Schramm et al.

(10) Patent No.: US 7,323,599 B2
(45) Date of Patent: Jan. 29, 2008

(54) PROCESS FOR REDUCTIVELY AMINATING KETONES AND ALDEHYDES WITH AQUEOUS AMINES AND CATALYSTS SUITABLE THEREFOR

(75) Inventors: Daniel Schramm, Sulzbach (DE); Daniel Decker, Liederbach a. Ts. (DE); Klaus Forstinger, Babenhausen (DE); Klemens Flick, Heilbronn (DE)

(73) Assignee: Clariant Speciality Fine Chemicals (Deutschland) GmbH, Frankfurt am Main (DE)

( * ) Notice: Subject to any disclaimer, the term of this patent is extended or adjusted under 35 U.S.C. 154(b) by 0 days.

(21) Appl. No.: 11/526,337

(22) Filed: Sep. 25, 2006

(65) Prior Publication Data

US 2007/0078282 A1    Apr. 5, 2007

(30) Foreign Application Priority Data

Oct. 1, 2005    (DE)    ............. 10 2005 047 288

(51) Int. Cl.
*C07C 209/00*    (2006.01)

(52) U.S. Cl. .................................... 564/471

(58) Field of Classification Search ............. 556/466; 564/471
See application file for complete search history.

(56) References Cited

U.S. PATENT DOCUMENTS

| 4,952,734 A | 8/1990 | Weber |
| 5,011,996 A | 4/1991 | Kiel |
| 5,055,618 A | 10/1991 | Kampmann et al. |
| 6,462,236 B2 | 10/2002 | Liang |
| 2001/0003136 A1 | 6/2001 | Nouwen et al. |
| 2002/0082455 A1 | 6/2002 | Liang |

FOREIGN PATENT DOCUMENTS

GB    969977    9/1964

OTHER PUBLICATIONS

Houben-Weyl, Meth. Der Chemie, 4. Auflage, Bd IV/1c, Reduktion Teil1, Thieme Verlag, 1980, pp. 436-437, Germany.
EPO Office Action for Corresponding Application No. 06019315.8 dated Dec. 27, 2006.

*Primary Examiner*—Samuel A Barts
(74) *Attorney, Agent, or Firm*—Foley & Lardner LLP

(57) ABSTRACT

A process for preparing amines of the general formula (I)

$$R^1R^2CHNR^3R^4 \quad (I)$$

in which $R^1$, $R^2$, $R^3$ and $R^4$ are each independently hydrogen, straight-chain or branched, halogenated or halogen-free $C_1$-$C_{12}$-alkyl, $C_3$-$C_{12}$-cycloalkyl, $C_6$-$C_{10}$-aryl or $C_7$-$C_{11}$-aralkyl, by catalytic, hydrogenating amination of carbonyl compounds of the general formula (II)

$$R^1\text{—}C(\text{=}O)\text{—}R^2 \quad (II)$$

with nitrogen compounds of the general formula (III)

$$HNR^3R^4 \quad (III)$$

in the presence of bifunctional catalyst systems comprising a.) a hydrogenation-active catalyst component comprising one or more metals of transition group 8 of the Periodic Table and b.) one or more solid, acidic cocatalysts, wherein the hydrogenating amination is carried out in the presence of aqueous ammonia or aqueous amine of the formula (III) and at least one organic solvent miscible with ammonia or the aqueous amine of the formula (III).

12 Claims, No Drawings

PROCESS FOR REDUCTIVELY AMINATING KETONES AND ALDEHYDES WITH AQUEOUS AMINES AND CATALYSTS SUITABLE THEREFOR

The reductive amination of ketones and aldehydes is a method customary in industry for preparing amines from aldehydes or ketones. The reaction is carried out on the industrial scale always in an excess of anhydrous ammonia in order to prevent the formation of secondary amines and to ease the formation of the imine which occurs as an intermediate. The imine is formed by an addition of an ammonia to the carbonyl group and subsequent elimination of water. In aqueous media, the equilibrium of the elimination reaction is well to the side of the reactants.

The reaction was typically carried out in the presence of metallic catalysts. The catalysts used are, for example, Raney Ni, Raney Co, Pt/C, Pd/C, Pd/BaSO$_4$ or Rh/Al$_2$O$_3$. Houben-Weyl, Methoden der Organischen Chemie [Methods of organic chemistry], 4th ed., Vol. IV/1c, Reduktion Teil 1 [Reduction part 1], Thieme Verlag, 1980, pages 436-437 states that haloaromatics are not attacked in the course of the hydrogenating amination with Raney nickel. Two illustrative reactions are specified, but lead to low yields. Presumably, dehalogenation occurs as a significant side reaction in the examples cited.

GB-A-969 977 describes substituted 1,3-diphenylpropylamines and corresponding imines. Example 6 describes the hydrogenating amination of 1-(2-ethyl-4,5-dimethoxyphenyl)-3-(4-chlorophenyl)-1-propenol with ammonia with a Raney Ni as a catalyst. After the workup, 1-amino-1-(2-ethyl-4,5-dimethoxyphenyl)-3-(chlorophenyl)propane hydrochloride is obtained as the product.

EP-A-355 351 relates to a process for preparing amines by reductively aminating oxo compounds which contain halogen-substituted aromatic substituents. The reaction is carried out in particular over Raney Ni or Raney Co in the presence of ammonia or amines. In addition, the reaction is carried out in the presence of organic sulfur compounds such as dimethyl sulfoxide or bis(2-hydroxyethyl) sulfide. The organic sulfur compound is used in amounts of preferably from 1 to 25% by weight based on the catalyst. In relation to the carbonyl compound, amounts of more than 1% by weight are present. The sulfur compounds serve to partially poison the catalyst, so that the aromatically bonded halogen can be obtained. For example, in the case of amination of p-chloroacetophenone under suitable conditions, yields of p-chlorophenylethylamine of up to 90% are achieved.

However, the addition of the relatively large amounts of sulfur compounds is disadvantageous in that a further component which can complicate the workup of the reaction products, especially by distillation, is introduced into the reaction system. In addition, the organic sulfur compounds cause higher catalyst consumption which is typically above 6% by weight of the Ni catalyst based on the carbonyl compounds used.

EP-A-1201642 therefore describes a process for preparing amines from halogenated aromatics with anhydrous ammonia. In order to prevent dehalogenation of the aromatic, a solid acidic cocatalyst is added. In Example 6, p-chloroacetophenone together with 1.6% by weight of Raney Co and 19% by weight of ZrO$_2$, based on the reactant, in methanol, is reacted with ammonia to give p-chlorophenylethylamine in >98% yield.

However, working in anhydrous systems, as described in the prior art, means a considerable level of process complexity, which makes the process uneconomic especially in the case of industrial scale preparation.

It is therefore an object of the present invention to provide a process for preparing amines by reductive amination of carbonyl compounds in aqueous ammonia solutions, which avoids the disadvantages of the known processes and leads to the desired amines in high yields with good selectivity and a simple procedure.

According to the invention, the object is achieved by a process for preparing amines of the general formula (I)

$$R^1R^2CHNR^3R^4 \tag{I}$$

in which $R^1$, $R^2$, $R^3$ and $R^4$ are each independently hydrogen, straight-chain or branched, $C_1$-$C_{12}$-alkyl, $C_3$-$C_{12}$-cycloalkyl, $C_6$-$C_{10}$-aryl or $C_7$-$C_{11}$-aralkyl, by catalytic, hydrogenating amination of carbonyl compounds of the general formula (II)

$$R^1\text{---}C(\!=\!O)\text{---}R^2 \tag{II}$$

with nitrogen compounds of the general formula (III)

$$HNR^3R^4 \tag{III}$$

in the presence of bifunctional catalyst systems comprising a.) a hydrogenation-active catalyst component comprising one or more metals of transition group 8 of the Periodic Table and b.) one or more solid, acidic cocatalysts, wherein the hydrogenating amination is carried out in the presence of aqueous ammonia and at least one organic solvent miscible with ammonia.

It has now been found that, surprisingly, carbonyl compounds, especially ketones and aldehydes, in aqueous reaction solutions comprising one or more nitrogen compounds, especially ammonia, in a concentration of from 0.1 to 80% by weight, in particular from 1 to 25% by weight, and an organic solvent miscible therewith, in the presence of hydrogen, can be converted to amines.

The solvents used for the process according to the invention may be polar protic solvents, for example alcohols such as methanol, ethanol, propanol or butanol, or else water or mixtures thereof with one another.

The solvent content of the reaction mixture is preferably in the range from 20 to 85% by weight, in particular from 30 to 70% by weight.

Carbonyl compounds of the formula (II) usable in accordance with the invention are, for example, acetophenone, methylacetophenone, F-acetophenone, benzaldehyde and F-benzaldehyde, 4,4'-dichlorobezophenone, to name just a few.

The nitrogen compounds of the formula (III) selected are preferably amines from the following group: ammonia, methylamine, ethylamine, propylamine, dimethylamine, diethylamine, dipropylamine. Preference is given to using ammonia. The nitrogen compounds of the formula (III) can simultaneously also serve as solvents.

The speed and selectivity of the reaction to give the desired amine is increased by the use of a bifunctional catalyst system (for example Pd/TiO$_2$ or Pd/C+TiO$_2$). The catalyst system is composed of one or more solid, acidic cocatalysts which contain an oxidic material which is capable of catalyzing imine formation and a hydrogenation-active catalyst component.

The cocatalysts used may in particular be acidic oxides such as Al$_2$O$_3$, TiO$_2$, SiO$_2$, Cr$_2$O$_3$, ZrO$_2$, in particular TiO$_2$, ZrO$_2$, or mixtures thereof.

The hydrogenation-active component comprises one or more elements of the transition metals of transition group 8 of the Periodic Table.

Preference is given to using Pd, Pt, Co, Ni, Ru and Rh or compounds thereof. The metals of the hydrogenation-active components may also be used mixed in any weight ratios and additionally comprise further metals, for example Fe, Mo, Cu, Ag, V, Zn, W, in fractions of from 0 to 5% by weight. In the process according to the invention, the catalysts are preferably used in the form of elemental metal, in the form of oxides or bound to supports. Examples thereof are Raney cobalt or Raney nickel, as metal sponge, elemental Pd, Pt, Rh, Ru, Ir on supports, for example C, $Al_2O_3$, $SiO_2$, $TiO_2$, $ZrO_2$, $BaSO_4$, MgO, $Cr_2O_3$.

The hydrogenation-active component is used in an amount of from 0.1 to 10% by weight, preferably from 1 to 5% by weight, based on the carbonyl compound to be aminated.

The cocatalysts may be used as a support for the hydrogenation-active component; it is equally possible to use both catalyst components in the form of a suspension.

The amination is carried out preferably at temperatures in the range from 30 to 200° C., in particular at temperatures in the range from 50 to 180° C., at a hydrogen pressure of from 1 to 100 bar, in particular from 2 to 80 bar.

The process according to the invention is preferably carried out in an autoclave; the hydrogenation may also be effected in a fixed bed.

The process according to the invention features a simple and economically viable process and at the same time allows the desired amine compounds to be prepared with high selectivities and good yields.

EXAMPLES

Example 1 (V32)

Conversion of methylacetophenone to the amine over Pd/C and $TiO_2$ 10 ml of methylacetophenone were mixed in an autoclave (from Berghoff) with 30 ml of concentrated aqueous ammonia solution (25% by weight), 40 ml of methanol and 500 mg of a commercial Pd/C catalyst (5% Pd on activated carbon, from AMC) and 500 mg of $TiO_2$ (VKR611, from Sachtleben). The reaction mixture was heated to a temperature of 84° C., then hydrogen was injected up to a total pressure of 5.5 bar. After a reaction time of 180 min, the autoclave was cooled and decompressed, and the reaction mixture was analyzed by gas chromatography. Methylacetophenone had been converted to an extent of 93.5%. The selectivity for the amine was 99.5%.

Example 2 (V59)

Conversion of methylacetophenone to the amine over Pd/C and $TiO_2$ 10 ml of methylacetophenone were mixed in an autoclave (from Berghoff) with 30 ml of concentrated aqueous ammonia solution (25% by weight), 30 ml of methanol and 1000 mg of a catalyst prepared by impregnating titanium dioxide powder (VKR611, from Sachtleben) with aqueous palladium nitrate solution. The catalyst had a Pd content of 3% by weight. The reaction mixture was heated to a temperature of 93° C., then hydrogen was injected up to a total pressure of 7 bar. After a reaction time of 180 min, the autoclave was cooled and decompressed, and the reaction mixture was analyzed by gas chromatography. Methylacetophenone had been converted to an extent of 94%. The selectivity for the amine was 94%.

Example 3

Conversion of acetophenone to the amine with aqueous ammonia over Pd/C+$TiO_2$ 10 ml of acetophenone were mixed in an autoclave (from Berghoff) with 30 ml of concentrated aqueous ammonia solution (25% by weight), 30 ml of methanol and 500 mg of a commercial Pd/C catalyst (5% Pd on activated carbon, from AMC) and 500 mg of $TiO_2$ (VKR611, from Sachtleben). The reaction mixture was heated to a temperature of 85° C., then hydrogen was injected up to a total pressure of 5 bar. After a reaction time of 3 h, the autoclave was cooled and decompressed, and the reaction mixture was analyzed by gas chromatography. Acetophenone had been converted to an extent of 78%. The selectivity for the corresponding amine was 97%.

Example 4

F-Benzaldehyde with Ni/support 15.3 g of a Ni/C catalyst (Kataleuna 6504 K) were suspended in 919 g of aqueous ammonia solution (27%) in a 2 l steel autoclave and admixed with 302.5 g of 4-fluorobenzaldehyde. After heating to 120° C., hydrogen was injected, the pressure being kept at 38-45 bar by metering in hydrogen repeatedly. After 2.5 h, the hydrogen absorption slows. The reaction is completed at 120° C. and at an initial pressure of 45 bar for 15 h. The autoclave is decompressed and the reaction mixture analyzed by gas chromatography. Composition of the crude solution (proportion extractable by $CH_2Cl_2$, anhydrous, GC [a/a]): 4-fluorobenzylamine 90.7%; benzylamine 0.4%, 4-fluorobenzyl alcohol 1.2%; di(4-fluorobenzyl)amine 1.8%; trimer (M=352) 1.4%, others 4.5%.

Comparative Example (V22)

Hydrogenation of methylacetophenone with aqueous ammonia over Pd/C without addition of $TiO_2$ 10 ml of methylacetophenone are mixed in an autoclave (from Berghoff) with 30 ml of concentrated aqueous ammonia solution (25% by weight), 20 ml of methanol and 500 mg of a commercial Pd/C catalyst (5% Pd on activated carbon, from AMC). The reaction mixture is heated to a temperature of 99° C., then hydrogen is injected up to a total pressure of 9.4 bar. After a reaction time of 70 min, the autoclave is cooled and decompressed, and the reaction mixture is analyzed by gas chromatography. Methylacetophenone had been converted to an extent of 99%. However, the selectivity for the amine was only 17.7%.

The invention claimed is:

1. A process for preparing amines of the general formula (I)

$$R^1R^2CHNR^3R^4 \quad (I)$$

in which $R^1$, $R^2$, $R^3$ and $R^4$ are each independently hydrogen, straight-chain or branched, halogenated or halogen-free $C_1$-$C_{12}$-alkyl, $C_3$-$C_{12}$-cycloalkyl, $C_6$-$C_{10}$-aryl or $C_7$-$C_{11}$-aralkyl, said process comprising catalytic, hydrogenating amination of a carbonyl compound of the general formula (II)

$$R^1-C(=O)-R^2 \quad (II)$$

with a nitrogen compound of the general formula (III)

$$HNR^3R^4 \quad (III)$$

in the presence of a bifunctional catalyst comprising a.) a hydrogenation-active catalyst component comprising a metal selected from the group consisting of Pt, Pd and mixtures thereof disposed on carbon and b.) one or more solid, acidic cocatalysts selected from the group consisting of $Al_2O_3$, $TiO_2$, $SiO_2$, $ZrO_2$, and mixtures thereof, wherein the hydrogenating amination is carried out in a reaction mixture in the presence of an aqueous solution being an aqueous ammonia or aqueous amine of the formula (III) and at least one organic solvent miscible with ammonia or the aqueous amine of the formula (III).

2. The process as claimed in claim 1, wherein the aqueous solution has an amine concentration in the range from 0.1 to 80% by weight.

3. The process of claim 1, wherein the one or more solid acidic cocatalysts provides support for the second hydrogenation-active catalyst component.

4. The process of claim 1, wherein the hydrogenation-active catalyst component and the one or more solid acidic cocatalysts are present in suspension.

5. The process of claim 1, wherein the carbonyl compound is selected from the group consisting of methylacetophenone, fluoroacetophenone, benzaldehyde, fluorobenzaldehyde, and 4,4'-dichlorobenzophenone.

6. The process of claim 1, wherein the nitrogen compound is selected from the group consisting of methylamine, ethylamine, propylamine, dimethylamine, diethylamine, dipropylamine, ammonia, and mixtures thereof.

7. The process of claim 1, wherein the at least one organic solvent is present in the reaction mixture in the, range from 20 to 85% by weight.

8. The process of claim 1, wherein the organic solvent miscible with amine is at least one polar protic solvent.

9. The process of claim 1, wherein the at least one solid acidic cocatalyst is selected from the group consisting of $TiO_2$, $ZrO_2$, and mixtures thereof.

10. The process of claim 8, wherein the at least one polar protic solvent is an alcohol or water or a mixture thereof.

11. The process of claim 6, wherein the nitrogen compound is ammonia.

12. The process of claim 1, wherein the hydrogenating amination is carried out in the presence of aqueous amine solution having a concentration in the range from 1 to 25% by weight.

* * * * *